US008359901B2

(12) United States Patent
Freund et al.

(10) Patent No.: US 8,359,901 B2
(45) Date of Patent: Jan. 29, 2013

(54) CHEMICAL IMPAIRMENT DETECTION SYSTEM AND METHOD OF USE TO REDUCE CIRCUMVENTION

(75) Inventors: Richard C. Freund, Cincinnati, OH (US); Thomas E. Knowles, Batavia, OH (US); Jason Niklas, Cincinnati, OH (US); Mitchell K. Neeld, Cincinnati, OH (US); Sherman Couch, Cincinnati, OH (US)

(73) Assignee: LifeSafer Interlock, Cincinnati, OH (US)

( * ) Notice: Subject to any disclaimer, the term of this patent is extended or adjusted under 35 U.S.C. 154(b) by 596 days.

(21) Appl. No.: 12/473,717

(22) Filed: May 28, 2009

(65) Prior Publication Data

US 2009/0293589 A1 Dec. 3, 2009

Related U.S. Application Data

(60) Provisional application No. 61/056,677, filed on May 28, 2008.

(51) Int. Cl.
*G01N 33/497* (2006.01)
(52) U.S. Cl. ........................................................ 73/23.3
(58) Field of Classification Search .................... 73/23.3
See application file for complete search history.

(56) References Cited

U.S. PATENT DOCUMENTS

| | | | | |
|---|---|---|---|---|
| 4,843,377 A * | 6/1989 | Fuller et al. | ................. | 340/573.4 |
| 4,916,435 A * | 4/1990 | Fuller | .......................... | 340/573.4 |
| 5,204,670 A * | 4/1993 | Stinton | ...................... | 340/573.4 |
| 5,222,152 A * | 6/1993 | Fishbine et al. | ............. | 340/5.83 |
| 6,018,739 A * | 1/2000 | McCoy et al. | .......................... | 1/1 |
| 6,748,792 B1 * | 6/2004 | Freund et al. | ................... | 73/23.3 |
| 6,956,484 B2 * | 10/2005 | Crespo | ........................... | 180/272 |
| 7,027,621 B1 | 4/2006 | Prokoski | | |
| 7,218,236 B2 * | 5/2007 | Mobley et al. | ................. | 73/23.3 |
| 7,425,978 B2 * | 9/2008 | Katz | ........................... | 348/14.01 |
| 7,451,852 B2 * | 11/2008 | Stewart et al. | ................ | 180/272 |

(Continued)

FOREIGN PATENT DOCUMENTS

EP 1591296 A 11/2005
EP 2075151 A 7/2009

(Continued)

OTHER PUBLICATIONS

International Search Report, (PCT US 09/45468), International Filing Date May 28, 2009.

(Continued)

*Primary Examiner* — Lisa Caputo
*Assistant Examiner* — Punam Roy
(74) *Attorney, Agent, or Firm* — Wood, Herron & Evans, LLP

(57) ABSTRACT

A chemical impairment detection system and method of use comprising a video surveillance system adapted to record a facial image of a tester, the video surveillance system having a camera with a lens having a field of view from which the camera views images and distinguishes whether those images have appropriate construction or contrast of light intensity. The invention further comprises a control and relay module having a proper view and position determiner adapted to determine whether the facial image of the tester is properly positioned within the field of view during a chemical impairment detection test, and a test prompter to alert the tester when to begin the chemical impairment detection test. The present invention further comprises a chemical impairment detection sampling device in operable communication with and responsive to the video surveillance system, the sampling device adapted to receive a chemical impairment detection test sample from the tester.

22 Claims, 9 Drawing Sheets

U.S. PATENT DOCUMENTS

| | | |
|---|---|---|
| 7,481,292 B2 * | 1/2009 | Mobley et al. ............... 180/272 |
| 7,812,712 B2 * | 10/2010 | White et al. ................. 180/272 |
| 7,823,681 B2 * | 11/2010 | Crespo et al. ............... 180/272 |
| 2006/0237253 A1 * | 10/2006 | Mobley et al. ............... 180/272 |
| 2007/0144812 A1 | 6/2007 | Stewart et al. |
| 2008/0106390 A1 * | 5/2008 | White ..................... 340/426.11 |
| 2008/0252412 A1 * | 10/2008 | Larsson et al. ............... 340/5.2 |
| 2011/0050407 A1 * | 3/2011 | Schoenfeld et al. ..... 340/426.11 |

FOREIGN PATENT DOCUMENTS

| | | |
|---|---|---|
| GB | 2431496 A | 4/2007 |

OTHER PUBLICATIONS

European Search Report, Appl. No. 09007149.9-2319, mailed Sep. 15, 2009.

* cited by examiner

CHEMICAL IMPAIRMENT DETECTION SYSTEM AND METHOD OF USE TO REDUCE CIRCUMVENTION

FIELD OF THE INVENTION

The present invention relates to chemical impairment detection systems and their methods of use to reduce circumvention of the devices. One common such device is a sobriety interlock which is connectable to machinery or a vehicle, such as a car or a truck, and which normally operates to disable the machinery or vehicle from starting if it is determined, through the delivery of a breath alcohol test, that the intended user has recently consumed alcohol. More particularly, the present invention relates to a chemical impairment detection device which is adapted to facilitate the positive identification of the person who takes an impairment test. Such tests may be required before someone is allowed to start a vehicle or may be required at other times, whether while driving, at home, or at work.

BACKGROUND OF THE INVENTION

The operation of motor vehicles by individuals who are chemically impaired by alcohol or another substance is a major safety problem. Many automobile accidents involve someone that is under the influence of alcohol and in some cases, individuals who have already been cited or otherwise identified as misusing or abusing alcohol. In addition to putting the impaired driver at an increased risk of injury or death, the operation of a vehicle while under the influence of alcohol often also affects the safety of others, such as the drivers and passengers in other vehicles. In addition to the increased risk of serious bodily injury or death caused by someone who is driving while under the influence of a chemical substance, there is also an increased risk of serious damage to personal and real property, as well as the cost and potential distraction from other needed services associated with the law enforcement and rescue workers that are called upon to respond to such accidents.

Recognizing the seriousness of driving while under the influence, many laws have been written prohibiting such conduct and providing various methods for dealing with such offenses when they occur. For example, a court or licensing authority may suspend the driving privileges of someone who is convicted of driving while under the influence of alcohol or may require that a breath alcohol ignition interlock device be installed in his or her vehicle. Additionally, a state may require repeat offenders to install such devices as a condition of having their license reinstated.

Chemical impairment detection devices are also used to monitor and detect whether someone has improperly or without authorization consumed alcohol or drugs. For example, abstinence from the use of any alcohol may be a condition of a repeat offender's parole, probation, or home confinement.

A sobriety interlock device, when installed in an individual's vehicle, requires that the individual pass a sobriety test before the vehicle can be started. However, since the use of impairment detection interlocks is normally done outside the presence of law enforcement or any other supervising authority, and since a penalty may be attributed to a failed test, e.g., the vehicle will not start and a condition of parole may be violated, there can be a temptation to tamper with the impairment detectors to attempt to fraudulently affect its results. For example, if the designated tester has been drinking, he or she could ask someone who is sober to take the test for them and thus circumvent the interlock. Hence, a sobriety interlock that uses a breath sample to determine intoxication could be compromised if someone who is not intoxicated, like a child, provides the sample. Alternatively, an air compressor, balloon, or other like source of forced air may be blown into a sampling device in an attempt to circumvent the interlock. Once such a clean sample is provided, and the vehicle starts, the impaired driver can then drive away. Accordingly, there is a need to facilitate the identification of who is taking the test and whether the tester passed or failed in order to minimize circumvention and allow for the imposition of appropriate sanctions for violations.

Additionally, when a term of probation, parole, or home confinement requires alcohol or other chemical abstinence, or prohibits a person from attempting to operate a vehicle after consuming any alcohol, or after being impaired by alcohol, failing a breath test can result in serious penalties, including, for example, incarceration. However, with past systems, when a test detected prohibited levels of alcohol, the intended tester, e.g., the operator of the vehicle, could simply argue that someone else took and failed the test and thus altogether avoid the legal consequences, such as incarceration, and/or create evidentiary or proof issues requiring further and potentially costly adjudication.

To deter fraudulent testing or circumvention some systems require random retesting while the vehicle is in operation. However, just as a sober individual, like a child, can fraudulently take the initial test before the vehicle is allowed to start, that same individual could also ride along with the driver and fraudulently take a driving retest. Similarly, the designated tester could, as they may have initially done, use an air compressor, balloon, or other like source of clean forced air to circumvent the test. Additionally, some systems require a user to perform a certain identifying act, such as a sequence of blows. However, breath pulse codes can be copied by others or mimicked by using a forced air device and, as such, do not provide definite proof of the identity of the impairment tester.

As mentioned, chemical impairment detection systems are also used in conjunction with home confinement, or during an individual's probation. For example, as a term of probation, or as a term of a home confinement sentence, an individual may be required to abstain from the consumption of any alcohol and to periodically take a test for alcohol consumption. However ankle bracelets that measure alcohol off of the skin are cumbersome, costly, take a long time to gather a positive test result, and are not as accepted as benchmarked breath testing devices. Accordingly, a similar situation develops in that the identity of the user providing the sample must be positively confirmed. In an attempt to monitor and provide positive identification of the individual providing the sample, video cameras have been used. However, such monitoring can be less than desirable due to the amount of storage required by a video stream, the bandwidth required for transmission of such a video stream, the availability of reliable and adequate communications medium, whether wired, optical, or wireless, and the requirement for a human monitor to review the video stream. Also, the in home systems used for alcohol abstinence are typically not designed to be portable and generally cost more to operate than vehicle interlock systems. Moreover, the use of a camera in an automobile, or in a home for identification or even simply for recording an image, can further be hindered due to adverse lighting conditions, obstructions, movement, or poor camera angles. In other words, there can be issues regarding whether the tester will be visible, i.e., within the field of view of the camera and whether the camera will be able to capture an identifiable image of the tester.

Accordingly, there is a need for a detection device to enable positive identification of the individual who is subject to an impairment analysis. There is also a need for an impairment detection device that can desirably archive the requisite data to positively identify the impairment tester. There is also a need to deter circumvention of impairment detection systems. There is also a need to provide a low cost system for abstinence monitoring systems.

OBJECTS OF THE INVENTION

It is an object of the applicant's invention to improve the identification of the user of a chemical impairment detection device. It is also an object of the applicants' invention to deter easy circumvention of a chemical impairment detection or interlock system. It is another object of the applicants' invention to provide an improved impairment detection device for use in parole, probation, home confinement, or in other like situations, particularly those involving adverse lighting conditions and the like. It is also an object of the applicants' invention to both be a monitor for abstinence and to prevent drunk driving.

SUMMARY OF THE INVENTION

The present invention achieves these objects and overcomes the foregoing and other shortcomings and drawbacks of chemical impairment detection and interlock systems and methods heretofore known. The present invention comprises a video surveillance system that is in control of the testing process and is adapted to record a facial image of a tester, the video surveillance system having a camera with a lens having a field of view from which the camera views images and distinguishes whether those images have appropriate construction or contrast of light intensity. The invention further comprises a control and relay module having a proper view and position determiner adapted to determine whether the facial image of the tester or driver is properly positioned within the field of view during a chemical impairment detection test, and a test prompter to alert the tester when to begin the chemical impairment detection test. The present invention further comprises a chemical impairment detection sampling device in operable communication with and responsive to the video surveillance system, the sampling device adapted to receive a chemical impairment detection test sample from the tester.

The present invention also comprises a method for conducting a chemical impairment detection test comprising surveying a chemical impairment detection test site location with a video surveillance system, the video surveillance system having a camera with a lens having a field of view from which the camera views images for appropriate construction or contrasts of light intensity. The present invention further determines whether a facial image of a tester is properly distinguishable and positioned within the field of view during the chemical impairment detection test. The present invention also prompts the tester to provide a chemical impairment detection sample into a chemical impairment detection sampling device. Finally, the present invention records the facial image of the tester.

The present invention also comprises a method for reducing circumvention of a chemical impairment detection test comprising the steps of turning the ignition switch of a vehicle to the on position, activating a video surveillance system, and ensuring that a camera, located in the video surveillance system is at a proper operating temperature. The method further includes the steps of detecting that a position reference is distinguishable and located within a field of view of the camera, prompting a tester to begin blowing into a hand-held breath-alcohol sampling and analyzing device, and recording a facial image of the tester during the chemical impairment detection test. The method also has the steps of analyzing whether the position reference remains within the field of view of the camera during the chemical impairment detection test, determining whether the tester provided a requisite breath-alcohol sample, and evaluating the breath-alcohol content of the breath-alcohol sample from the tester. The inventive method additionally includes the steps of communicating to a vehicle ignition interlock whether to allow the tester to start the vehicle, monitoring the tester during the operation of the vehicle, and recording an image of the tester during the operation of the vehicle. Finally, this inventive method also comprises the steps of alerting the tester of a time window during which a chemical impairment detection retest must be commenced and communicating the results of the chemical impairment detection test and the facial image of the tester to an external receiver.

The above and other objects and advantages of the present invention shall be made apparent from the accompanying drawings and the descriptions thereof.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

DETAILED DESCRIPTION OF THE INVENTION

Figure 1:
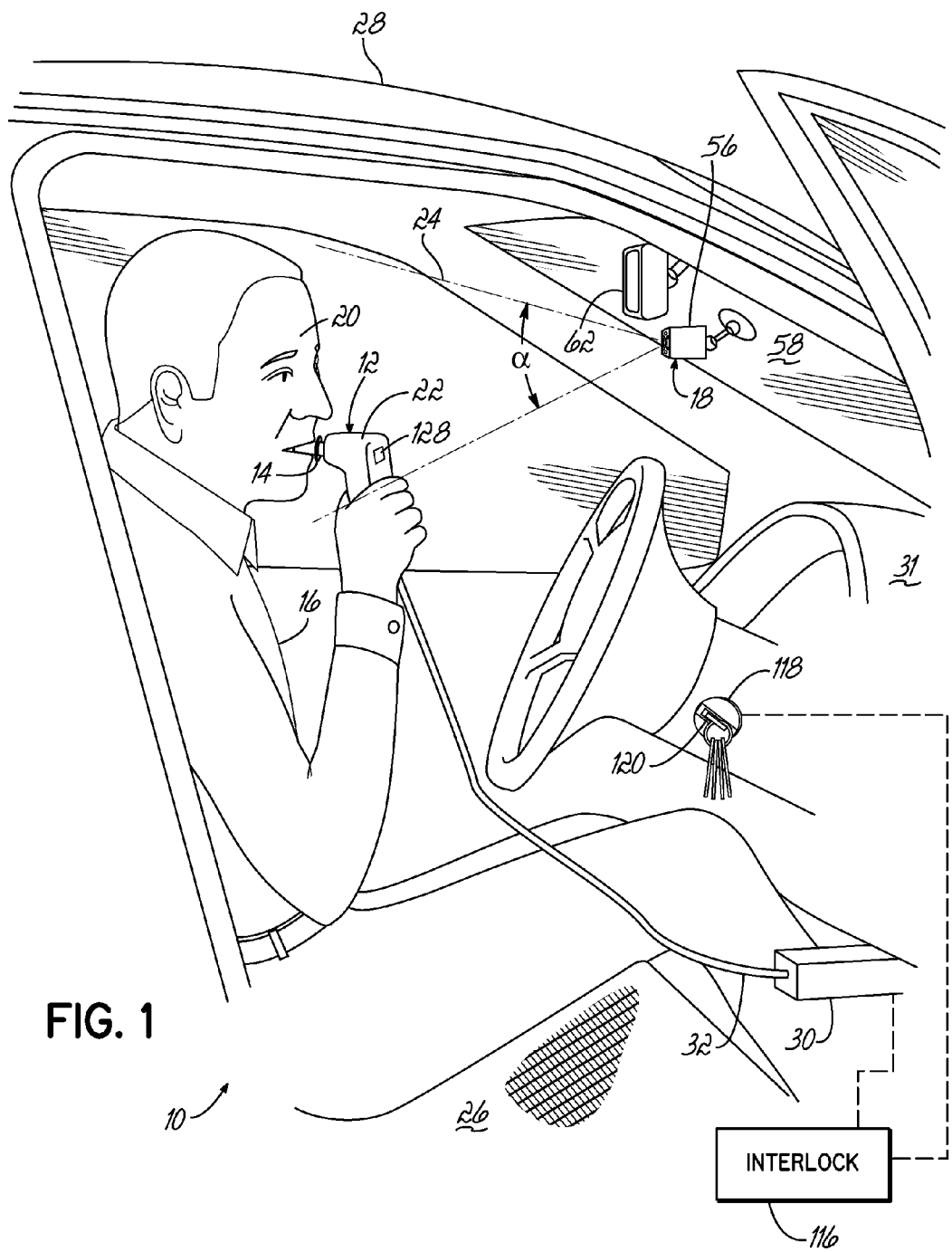
FIG. 1 is a perspective view of an embodiment of a chemical impairment detection system according to the present invention.

As shown in FIG. 1, the system 10 includes a chemical impairment detection sampling device 12 that is in operable communication with and responsive to a video surveillance system 18. In one embodiment, the hand-held device 12 is adapted for sampling a user's 16 breath through a mouthpiece 14 through which a user 16 provides a breath sample. The mouthpiece 14 may be disposable and can be configured so as to be required to be locked in the device 12 before a test can be taken. The mouthpiece 14 may also be constructed of a material, such as hard plastic, that will be resistant to bending.

To determine a user's 16 blood-alcohol content (BAC) from his or her breath, breath-sampling devices 12 typically require a "deep-lung" breath sample. Hence, the air that must be blown into the mouthpiece 14 generally must comprise alveolar air, which occurs when an expiratory breath substantially exhausts the lungs. Since breath expired from upper portions of the respiratory tract does not necessarily have an alcohol level proportional to that of the bloodstream, the breath-sampling or breath testing device 12 is adapted so as to prevent the processing of shallow exhalations, e.g., when a user 16 blows only short puffs of air expelled from the upper portions of his or her respiratory tract. One embodiment of the present invention ensures that a proper air sample will be given by including a pressure sensor in the device 12, which can determine when a deep-lung breath has been given. Typically, a user 16 is required to blow and hum for about 5 seconds.

The system 10 also includes a video surveillance system 18 positioned and adapted so as to have a camera angle α, which captures the identifying facial features 20 of a user 16 during a chemical impairment test. In alternative embodiments, the identifying facial features 20 of the user 16 may be captured via three dimensional (3D) facial geometry and topography techniques known to those skilled in the art. In addition, the video surveillance system 18 further captures at least a portion 22 of the hand-held sampling device 12 and mouthpiece 14 to positively link the impairment sample received and analyzed with the impairment tester 16. In other words, this prevents easy circumvention by simply handing the handset 12 out of view of the camera, e.g., out the car window or to a passenger. The field of view 24 of video surveillance system 18 may also be such as to sufficiently record the location of the user 16 during the impairment test, e.g., whether he or she is sitting in the driver's seat 26 of the vehicle 28, or sitting at home in view of the camera.

The hand module 12 has a microprocessor and memory to log event information and has various programmable options to determine its functionality. It is typically connected to a control/relay module (CRM) 30, generally located under the dashboard 31, via a coiled cord 32. In one embodiment, the hand module 12 weighs approximately 177 grams and is approximately is 15.25×5×3.8 cm in size. The control/relay module 30 weighs approximately 347 grams and is approximately 5×7.6×4.5 cm. The hand and relay modules 12, 30 will typically operate between −40° C. to 85° C. and between 10% to 90% relative humidity. With regard to accuracy, the hand module 12 will return a test result with a margin of error of ±0.005 g % between a BAC range of 0.010% to 0.10% and between a temperature of −40° C. to 70° C. Additionally, any embodiment which is adapted for use in vehicles will also be adapted to meet automobile vibration standards known to those skilled in the industry.

Figure 2:
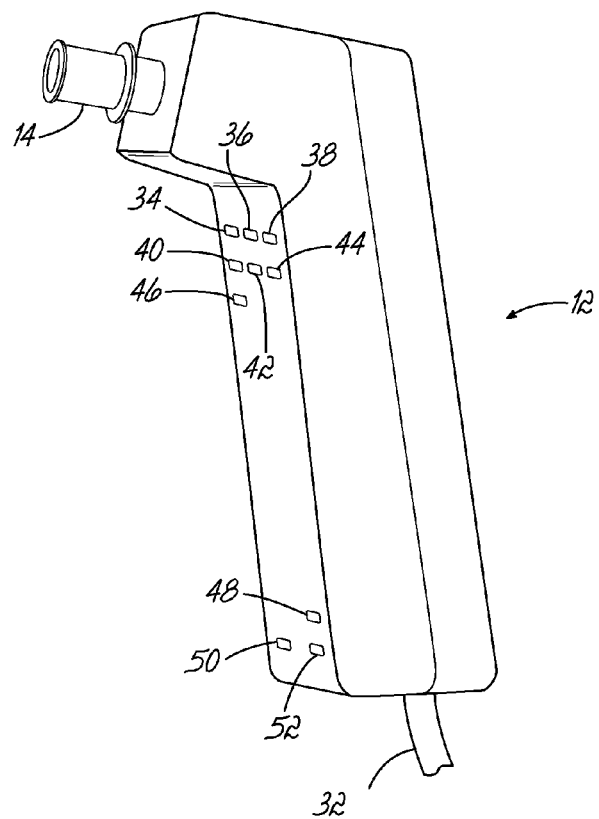
FIG. 2 is a perspective view of an embodiment of a handset of the chemical impairment detection system as shown in FIG. 1.

As shown in FIG. 2, the hand module 12 of that embodiment contains a plurality of LED's for communication with a user 16. These may include a blow light 34, a wait light 36, an abort light 38, a pass light 40, a warn light 42, a fail light 44, a run light 46, a service light 48, a power light 50, and a lockout light 52. The hand module 12 also contains an electrochemical fuel cell sensor to facilitate the processing and analysis of an alveolar air breath sample.

Figure 3:
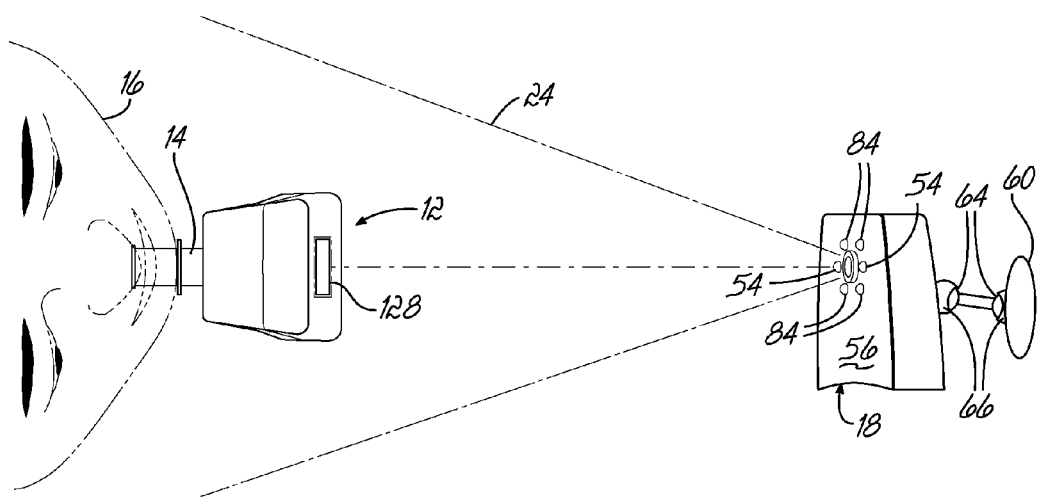
FIG. 3 is a top perspective view of an embodiment of the handset and video camera of the chemical impairment detection apparatus as shown in FIG. 1.

As shown in FIG. 3, the video surveillance system 18 of that embodiment also contains a plurality of LED's 54 (typically at least a red LED and a green LED) for communication with a user 16. The video surveillance system 18 further comprises a test prompter which could be in the form of an audio signal or LED 54 to alert the tester 16 when to begin the chemical impairment test. As shown, the video surveillance system 18 also contains a plurality of infrared (IR) LEDs 84.

As shown, the housing 56 for the video surveillance system 18 is separately and securely mounted to the windshield 58 with a suction cup mount 60 near the rearview mirror 62 in such a way as to not obstruct the driver's 16 view. A plurality of ball 64 and socket 66 adjustments may be used to enable the housing 56 to be positioned at the right height and angle to focus the video surveillance system 18 on the designated driver 16 in the designated vehicle 28. Other mounting mechanisms known to those skilled in the art may also be utilized, particularly if it is desired to mount the housing 56 on the dashboard, on the rear-view mirror, or at some other location in the vehicle 28. The housing 56 is typically plastic and is preferably tamper-sealed to further the reliability and integrity of the impairment test process.

Figure 4:
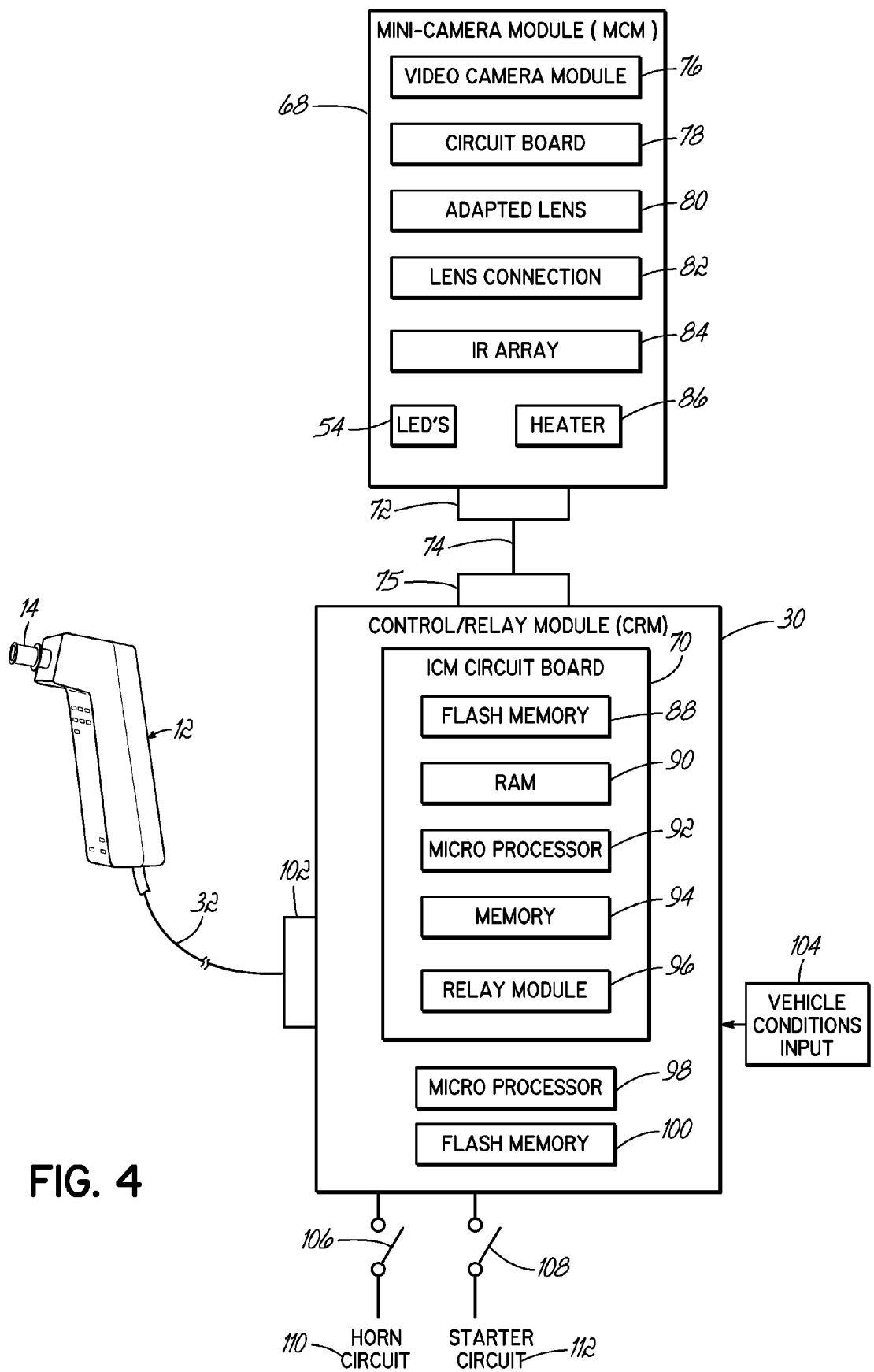
FIG. 4 is a block diagram of an embodiment of the present invention as shown in FIG. 1.

As shown in FIG. 4, the video surveillance system 18 of that embodiment is comprised of a mini-camera module (MCM) 68 and an intelligent camera module (ICM) 70. The intelligent camera module circuit board 70 is positioned within the control/relay module (CRM) 30 and is connected to the mini-camera module 68 via a serial port connector 72, a flexible and disconnectable serial cable or cord 74, and a disconnectable connector 75. In alternative embodiments, the mini-camera module 68 and the intelligent camera module could be wirelessly connected or even co-located in the same housing 56. The mini-camera module 68, generally comprises a video camera module 76, a circuit board 78, an adapted lens 80, a lens connector 82, an infrared (IR) array 84, LEDs 54, and a heater 86.

The intelligent camera module 70 generally comprises flash memory 88, RAM 90 for temporarily saving images streaming from the mini-camera module video, a microprocessor 92, memory 94 capacity to generally save at least 2,000 images, and a relay module 96. The intelligent camera module 70 is a separate system laid out on a common circuit board within the control/relay module 30 which is generally housed in an extruded aluminum case with faceplates with cut-outs on both ends for cabling.

The control/relay module 30 generally also has a microprocessor 98, flash memory 100, and mechanical relays 106, 108 which interface with the vehicle's 28 horn and starter circuits 110, 112. The control/relay module 30 generally is hardwired into the vehicle 28 and the relays 106, 108 are open in a sleep state and interrupt the horn and starter circuits 110, 112 before the vehicle 28 is started. The horn circuit 110 continues to remain interrupted unless needed to sound to alert an individual 16 that a test is required or to sound an alarm if there has been a test violation, such as could occur during a random moving. Programmable options and a vehicle status input 104 enable the control/relay module 30 to monitor vehicle 28 conditions like tachometer, voltage, or alternator reading to determine whether the vehicle 28 is started, idling, or moving. The control/relay module 30 also monitors and records whether the handset 12 is connected during these various vehicle conditions. For example, the control/relay module 30 would record a "No Blow" event whenever the vehicle 28 is determined to be running and the handset 12 was disconnected. The control/relay module 30 is connected to the handset 12 via a 4 pin DIN connector 102 and the cord 32. In alternative embodiments, the control/relay module 30 and the handset 12 may be wirelessly connected. The control/relay module 30 is preferably disconnectable from the vehicle's installed wiring harness for ease of replacement.

The control/relay module 30 further comprises programmed code that is adapted to distinguish whether the images seen by the camera lens 80 have the appropriate construction or contrasts of light intensity. The control/relay module 30 further comprises programmed code that is adapted to determine whether the facial image 20 of the tester 16 is properly positioned within the field of view 24 during a chemical impairment detection test. The position determiner program code is further adapted to sense, track, and analyze a positioning reference or target 128 within the field of view 24 during and throughout the chemical impairment detection test and can cancel or abort the test in the event that the target 128 is lost from the field of view 24 before the test is completed. In some embodiments, the position determiner program code may receive inputs from infrared sources, radio frequency sources, sonar or sound sources, or other proximity sensors such as GPS and the like. These inputs and sensors may be located on or part of the video surveillance system 18 or located on the handset 12.

The chemical impairment detection system 10 may further comprise a test window alert, which could be in the form of audio, visual, or motion alerts, or some combination thereof, to alert the tester 16 of a time window during which the chemical impairment detection test must be commenced. Additionally, in some embodiments, the system 10 may further comprise a communication module in operable communication with an external receiver and adapted to facilitate the transfer of a chemical impairment detection test result and the facial image of the tester 16 to an external receiver, such as a monitoring facility.

Additionally, when the present invention is used in vehicular applications, the system 10 may also have a vehicle ignition interlock 116 that is in operable communication with the hand-held breath-alcohol sampling and analyzing device 12. Moreover, additional components, known in the industry, can be added to the system 10 to provide for added capabilities. For example, a global positioning system (GPS) (not shown) can be incorporated into the system 10, whereby the exact location of the vehicle 28 when a violation occurred could be recorded. Such a capability may provide corroborating evidence of the tester's 16 identity, e.g., if the location happens to be in the tester's 16 garage 182, or may provide useful geographical information for legal jurisdictional purposes. Additionally, a system 10 that also has a wireless communication transmitter, e.g., a radio function, could be effective in notifying the monitoring facility or law enforcement of a failed impairment test. If the system 10 also had a GPS capability, law enforcement could be dispatched to the location of the vehicle 28 when there was a failed test. This capability could be extremely beneficial to intercept someone who is driving while impaired. Additionally, a system 10 with a wireless communication transceiver, e.g., cellular telephone, enabling two way communication, could also be used by the monitoring facility to dynamically order a recall of the system 10 or lock the ignition, in response to a violation. Finally, a system 10 with a wireless communication receiver could be used by a monitoring facility to dynamically request random alcohol tests.

Figure 5:
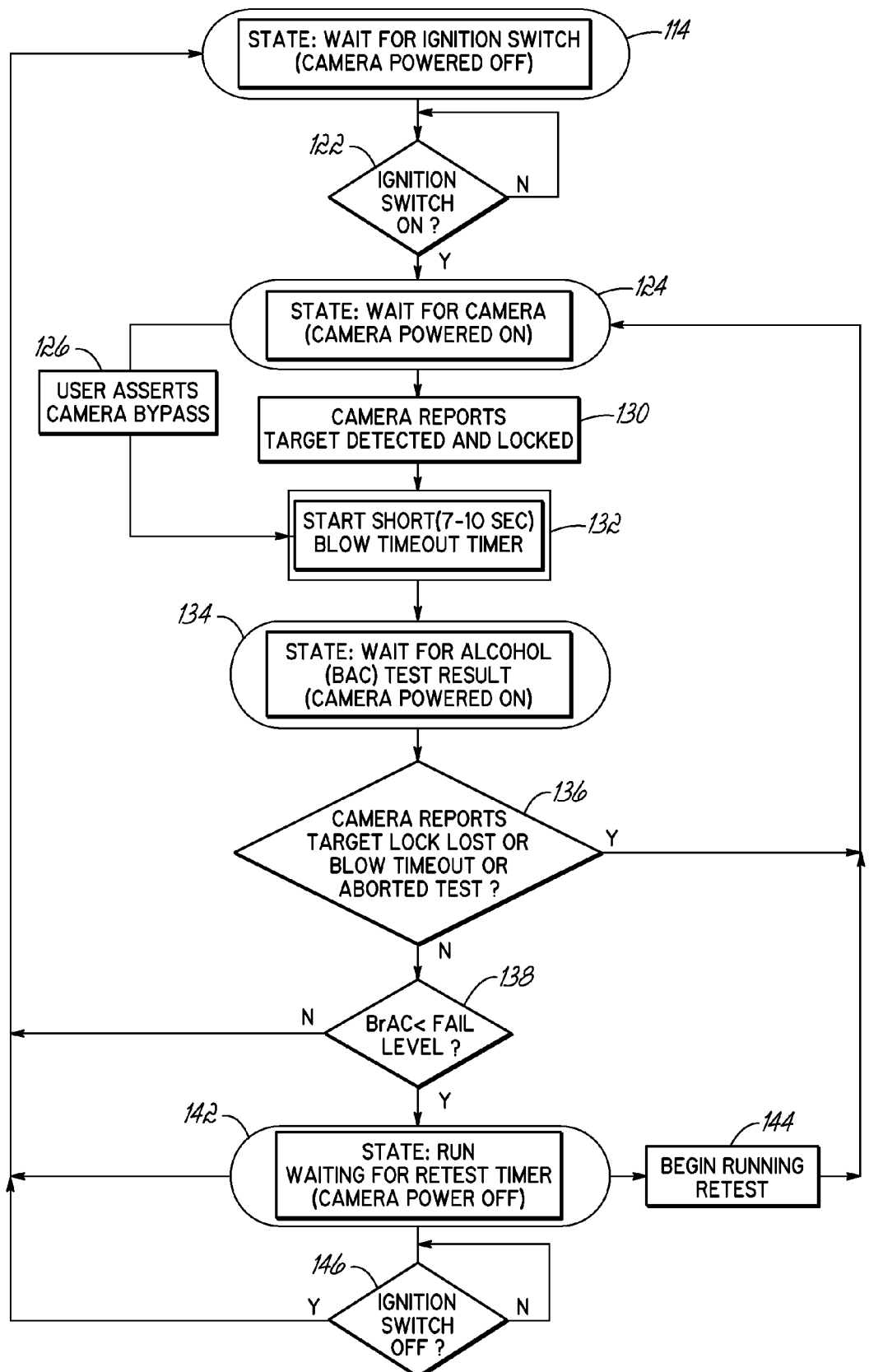
FIG. 5 is a flow chart of the process performed by an embodiment of the present invention.

FIG. 5 shows the operation of one embodiment of the present invention. At the beginning of the operational sequence (Block 114), power to the system 10 and the video surveillance system 18 is OFF. Power is provided to the system 10 when the driver 16 turns the key 120 and activates the vehicle's 28 ignition switch 118. Turning the key 120 ON also establishes the intent of the person 16 to operate the vehicle 28. Once the ignition switch 118 is on or activated (Block 122) an ignition switch input is provided to the system 10. The system 10 then waits for the sampling handset 12 and the video surveillance system 18 to warm-up (Block 124). The video surveillance system 18 must also burn-off any water condensation on the lens 80 which may arise in the automobile environment especially during time of rapid temperature changes associated mostly with overnight winter environments. The video surveillance system 18 must then detect the presence of a properly exposed image with sharp contrasts as opposed to an image with blurred contrasts produced by water condensation, or no image from either a blackout from the lens being covered, or a whiteout from a bright light such as a flashlight. If these conditions exist, the ICM 70 will tell the CRM 30 to alert the user 16, e.g. with a sound and/or a LED, to prepare to take a test.

Alternatively, a user 16 can bypass (Block 126) the video surveillance system 18 by toggling the ignition switch 118 three times ON/OFF before starting the vehicle 28. This instructs the system 10 to not require a picture in order to take an impairment sample. This feature allows for a user 16 to still provide an impairment sample and, if the sample is within the proper parameters, to still start the vehicle 28, even if the video surveillance system 18 malfunctions or fails.

The user 16 will be notified with a sound or light, e.g., a green LED 54, once the video surveillance system 18 detects (Block 130) the presence of a target 128. The target 128 is typically detected when the target's 128 borders are seen by the camera lens 80 in its entirety within a minimum and maximum diameter or area of light and dark surfaces. The target 128 may be a symbol such as a geometric figure (e.g., rectangle, triangle, circle, etc.), bar codes, identification (ID) cards, key fob dongles, labels with text, or the like which may be positioned or adhered to the rear of the handset 12. In some embodiments, the target 128 may have a discernible orientation, such as a 1×1½ rectangle, which could be used by the video surveillance system 18 to determine whether the handset 12 is properly positioned. In other embodiments, the target may be a part, portion of, or the handset 12 itself.

In addition to tracking the target 18, the video surveillance system 18 will also lock on to the target (Block 130) in order to keep the sampling handset 12 within the field of view 24 of the camera. This functionality deters circumvention from users 16 who may attempt to have another individual, other than the designated tester 16 from performing the impairment test.

In some embodiments, the video surveillance system 18 may capture a pre-test picture of the user 16. This may occur for example, after the target 128 has been tracked by the video surveillance system 18 for a certain period of time, e.g., a couple of seconds. After the picture is saved in the ICM memory 94, the user 16 is then prompted to begin a test.

Once the video surveillance system 18 prompts the user 16 to begin the impairment test, a blow timeout timer starts (Block 132). The system 10 then waits for the results of the analysis of the breath sample provided by the user 16, or for the blow timer to time out (Block 134). Typically, once the timer starts, a user 16 will typically have between approximately 7 to 10 seconds to provide a breath sample by blowing into the mouthpiece 14. The video surveillance system 18 will save an image (in some embodiments, a second image) of the user 16 providing a sample at a preset time from when it prompts the user 16 to begin the test. This image should capture identifiable features of the user's 16 face 20 while he or she is blowing into the handset 12. In a properly conducted test, the user 16 receives the test prompts from the mini-camera module 68 and as such must keep his or her focus directed towards the camera lens 80. If during the test window the video surveillance system 18 reports that the lock on the target 128 is lost, or the test is aborted, or the time for providing the sample expires (Block 136), the system 10 returns to the state where the video surveillance system 18 is powered on (Block 124). Thus, for example, if the tester 16 points the handset 12 down or the camera lens 80 away from his or her face 20 or does not hold the handset 12 steady so that the video surveillance system 18 loses sight of the target 128, the test will be aborted. A test will also be aborted if an analysis of the breath sample is not possible such as where the tester 16 fails to provide enough volume of breath to assure a deep lung sample to allow accurate testing.

If the user's 16 breath alcohol concentration (BrAC) is greater or equal to the fail level (Block 138) the system 10 records the failed test and returns to the state where the video surveillance system 18 is powered on (Block 124). The BrAC is an indication of the concentration of alcohol in a tester's 16 blood, as measured through a breath sample. In most states, 0.080% is defined as the legal limit for driving. Alternatively, if the user's 16 breath alcohol concentration is less than the fail level (Block 138), i.e., the BrAC value or above which the vehicle's starter circuit will be prevented from operation, the system 10 will allow the vehicle 28 to be started and power off the video surveillance system (Block 142). The system 10 will then begin running a retest timer (Block 144) to, at some random time in the future, turn the video system 18 on again (Block 124) and commence the testing sequence again. In alternative embodiments, the video surveillance system 18 will remain ON, but appear to be in a passive mode to the user 16. A rest is performed while the vehicle 28 engine is running to deter drinking while driving. Of course, if at any point the vehicle is turned off (Block 146) the complete start-up testing sequence is begun anew (Block 114).

Figure 6:
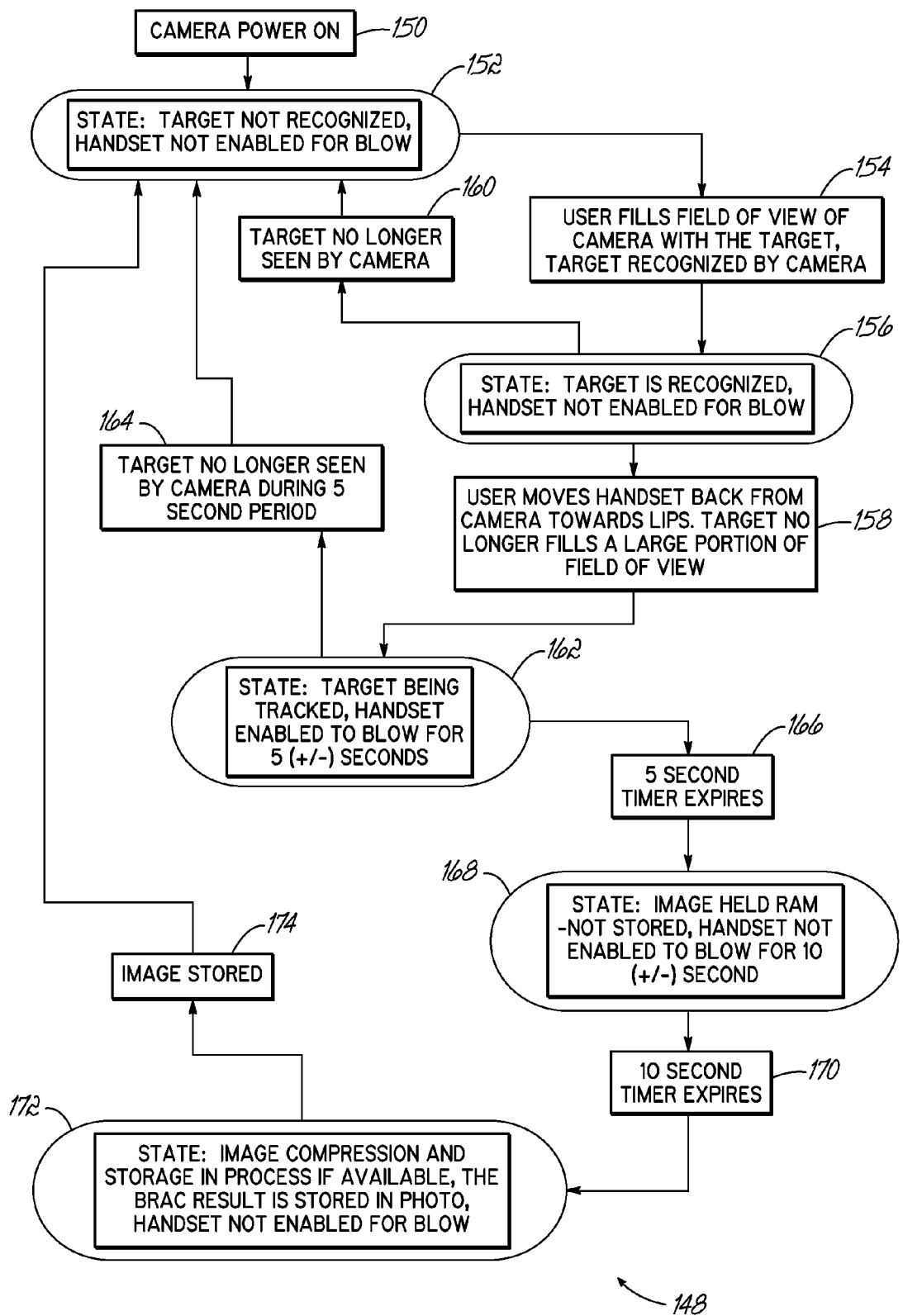
FIG. 6 is a flow chart of the process performed by an embodiment of the present invention.

FIG. 6 more particularly illustrates one embodiment of the target 128 tracking process 148 of the present invention. Target tracking is the capability of the system 10 to identify the sampling handset 12 and track the sampling handset 12 while it is in the video surveillance system 18 field of view 24. This allows the video surveillance system 18 to inform the sampling handset 12 when it has the sampling handset 12 in its field of view 24. The target 128 may be a passive object affixed to the sampling handset 12, such as a piece of black or white Velcro, which can also be used for mounting the handset 12. White Velcro may be preferable and somewhat easier to locate by the video surveillance system 18 in bright ambient lighting. Additionally, the target 128 may be 3M black reflective tape or other like reflective material which is designed to reflect light. Other types or forms of targets known to those skilled in the art may also be utilized.

To begin the target 128 tracking process 148, power is supplied (Block 150) to the video surveillance system 18. The target detection and tracking process 148 requires certain parameters than can vary with the varying lighting commonly found in the automobile environment. Accordingly, the video surveillance system 18 is designed to sense and adjust to those varying lighting conditions as needed.

Upon powering on (Block 150), the video surveillance system 18 will perform an auto exposure procedure whereby the optimum exposure settings will be determined based on the existing lighting conditions. Typically this is accomplished by placing the video camera module in an auto-exposure mode. Once these settings are determined, the video camera module 77 may then appropriately adjust the settings to enable the infrared array 84 to provide a usable reflective response from the target 128. Hence, for bright light conditions, the exposure settings may be adjusted so as to minimize the impact of the bright ambient light. In other words, the camera module 76 is placed into a fixed exposure mode with the exposure programmed to the calculated value.

Initially, the target 128 will typically not be recognized (Block 152) which in turn will not enable the handset 12 to receive a breath sample. To assist the video surveillance system 18 in acquiring the target 128, the user 16 may be trained to fill (Block 154) the field of view 24 of the video surveillance system 18 with the target 128. For example, the user 16 might place the handset 12 within 2 or 3 inches of the camera lens 80. This can be particularly helpful in allowing the video surveillance system 18 to acquire the target 128 when the foreground and/or background that is rich in detail, i.e., there is a cluttered image, such as may be the case in a home environment. However, this step may not be necessary in all embodiments of the present invention, such as those that use a highly reflective target, e.g., 3M reflective tape, or high definition camera lens.

In order for the video surveillance system 18 to determine whether the target 128 is in the field of view 24, the target detection algorithm uses a pulsed IR intensity delta technique for finding the target 128 in a field of view 24 that may contain multiple light sources. As the infrared array 84 begins pulsating emissions, the video surveillance system 18 is able to compare an image that corresponds to when the target 128 is illuminated by the infrared array 84, and when it is not. Sampling the field of view 24 first with the IR LEDs 84 on and then with the IR LEDs 84 off provides the method for identifying the presence of the highly reflective target 128 in the field of view 24. Multiple samples are used to filter out sporadic fluctuations in the lighting conditions. By comparing these images, the video surveillance system 18 is able to detect the presence of the target 128 when the handset 12 is properly positioned.

More specifically, the images are compared by counting the number of pixels in a specific region of interest (ROI) that exceed the previously calculated light intensity level when the IR LEDs 84 are on and when they are off. The difference or delta between the IR on pixel count and the IR off pixel count is then compared to a threshold valued (e.g., 10 percent) to determine if the target 128 is in the field of view 24. Typically the delta value must exceed the threshold value for four successive calculations for the target 128 to be detected.

Figure 7A:
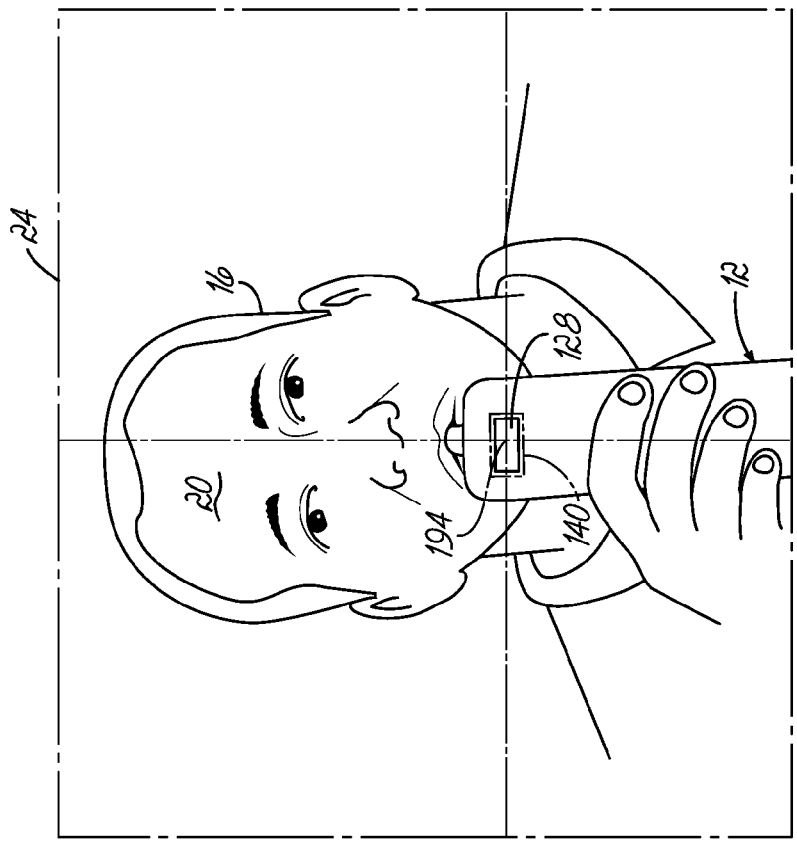
FIG. 7A is a view of an embodiment of a handset and use shown in FIG. 1 using the present invention.
Figure 7B:
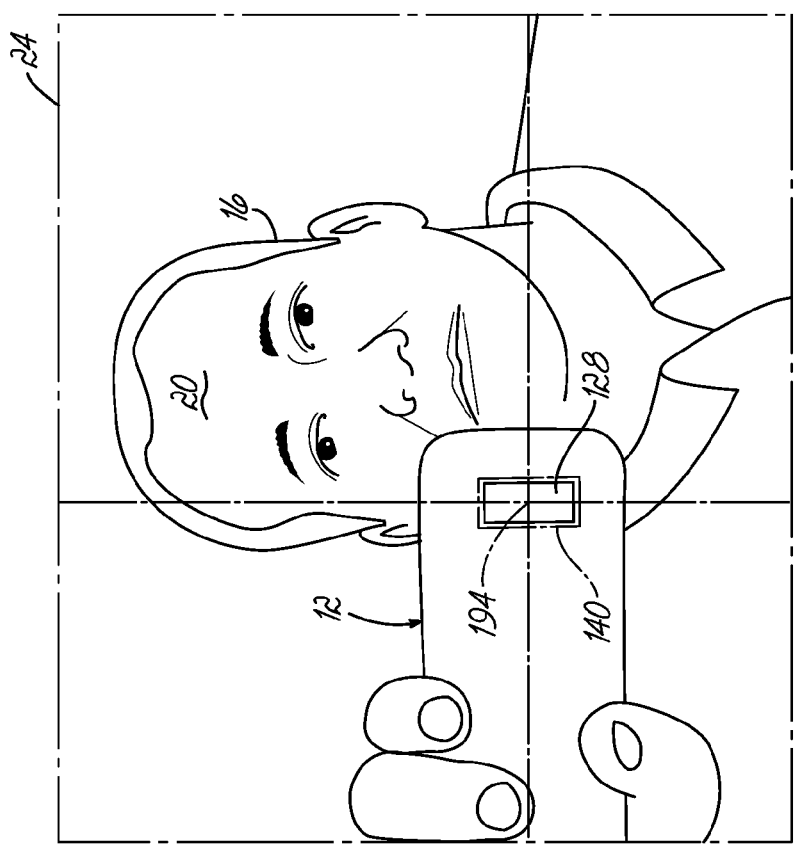
FIG. 7B is a view of an embodiment of a handset and use shown in FIG. 1 using the present invention.

In embodiments where the target 128 is placed close to the camera lens 80, once the target 128 is recognized (Block 156) the user 16 may pull the sampling handset 12 back away from (Block 158) the camera lens 80 and towards the user's 16 mouth in such a way as to keep the target 128 within the field of view 24 of the video surveillance system 18 to allow it to continued to be tracked by the video surveillance system 18. If at any time the target 128 becomes not visible (Block 160) to the camera lens 80, the process of target 128 acquisition (Block 152) begins again. Assuming the target 128 is not lost, the handset 12 is then enabled (Block 162) to receive a breath sample from the user 16 as shown in FIG. 7A. As shown in FIG. 7B, the video surveillance system 18 continues to track the target 128 during the test, which typically will take about 5 seconds. If at any time during the test the video surveillance system looses the target 128, i.e., the target 128 is no longer visible (Block 154), the target acquisition process (Block 152) begins again.

The target tracking algorithm uses a pulsed IR, difference image, center of gravity blob detect technique for tracking the target 128 in a potentially cluttered field of view 24. Mathematically subtracting the IR LED on image from the IR LED off image produces a difference image that enables the image of the target's 128 center of gravity 194 to be calculated. Additionally, this also allows for the image of the target's 128 geometry 140 to be analyzed which further aids in the accurate recognition of the target 128. Multiple samples may be used to prevent premature loss of the target due to either sporadic fluctuations in the lighting condition or momentary obstruction or removal of the target 128 from the field of view 24.

As with the target detection process, the target 128 is tracked by first setting the camera module 76 into the fixed exposure mode with the exposure programmed to the calculated value. Images are compared with the IR LEDs 84 on and off. A center of gravity analysis is performed on the difference between the two images that results in a set of coordinates identifying the center 194 of image of the target 128. Additionally, the shape 140 of the image of the target 128 is analyzed to determine if its aspect ratio is similar to that of the target 128, e.g. 1×1½. If the target is not found for four successive iterations, the target 128 is determined to be lost.

After the test time expires (Block 166), image(s) from the video surveillance system 18 are held in the RAM for about 10 seconds (Block 168). During this time the handset 12 is not enabled to receive a breath sample. After the designated time expires (Block 170) the images are compressed and along with the results of the breath test (Block 172) and stored (Block 174). Preferably, the BrAC result is stored in the photograph. Hence, the system 10 allows for recordation of a photograph of the user 16 blowing in the sampling handset 12. The process of target acquisition (Block 152) will then commence again for another test.

The chemical impairment detection system 10 further provides for the capability for conducting random driving retests. Such tests are important to detect whether a driver 16 has become impaired after his or her vehicle 28 has been started, such as could occur from the consumption of alcohol while driving. Once the retest timer 144 determines that a retest is needed, the video surveillance system 18 will silently record an image of the driver 16. This is done so as not to distract the driver 16 while the vehicle 28 is potentially in motion. The driver 16 will then be notified that a retest is required. In order to allow the driver 16 to have time to safely bring the vehicle 28 to a safe testing location, the driver 16 will typically have about 5-6 minutes to complete the retest. If the driver 16 chooses to ignore and refuse the retest, a retest refusal will be recorded and the secret image of the driver 16 captured will be associated with the violation event.

In some embodiments the video surveillance system 18 may conduct continuous surveillance of the driver 16 while the vehicle 28 is running and may sound an alarm if it fails to detect a proper image. It is preferable while the vehicle 28 is running to use audio signals as opposed to visual signals to communicate with the driver 16 to avoid potentially harmful distractions.

When it is time for a retest, the process of target 128 acquisition will commence as was the case prior to the start of the vehicle. Of course if any retest is failed, the images associated with that failed test will be stored for later use.

Figure 8:
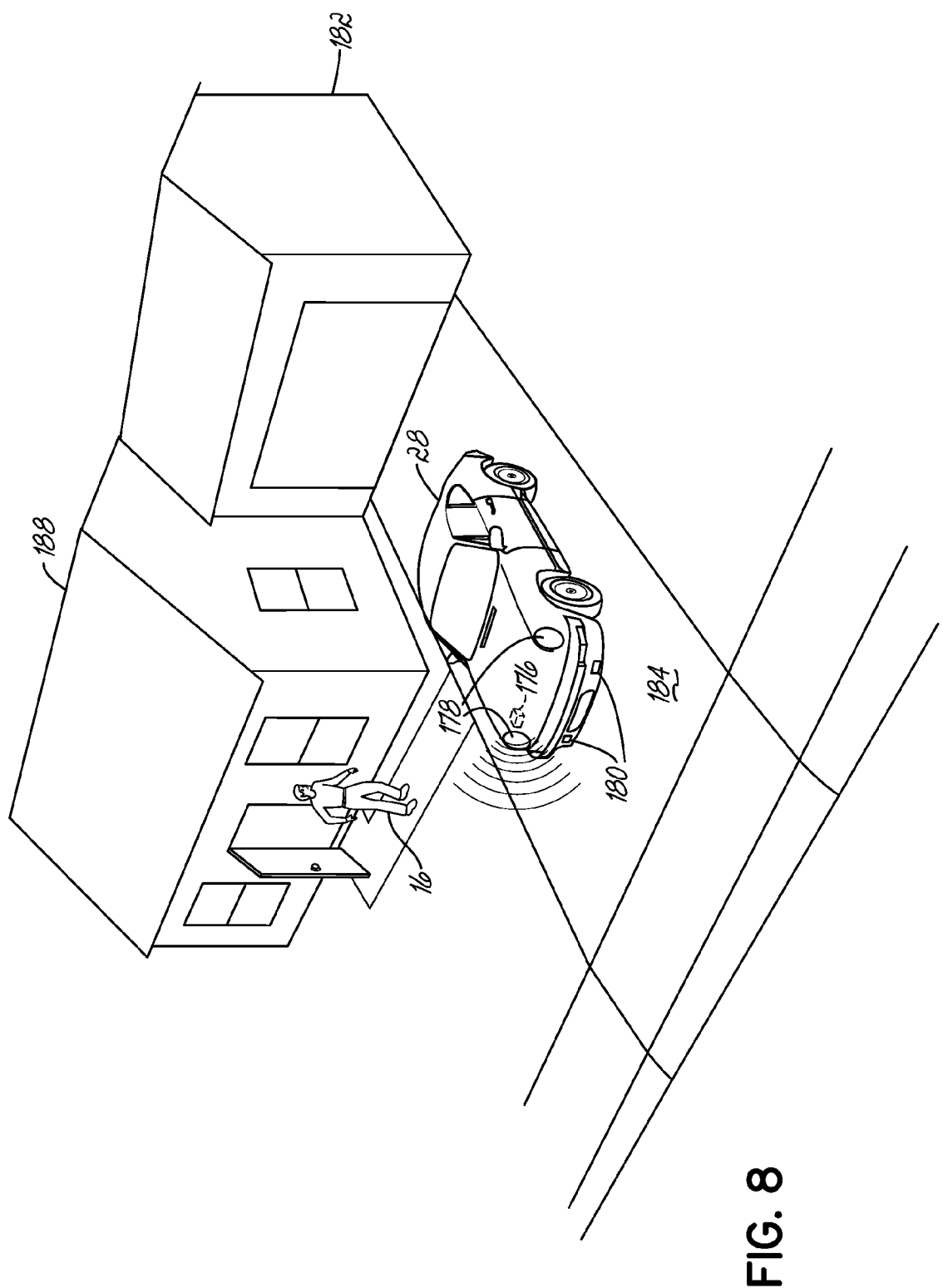
FIG. 8 is a perspective view showing the use of the present invention shown in FIGS. 1-4 in the context of a home driveway test.
Figure 9:
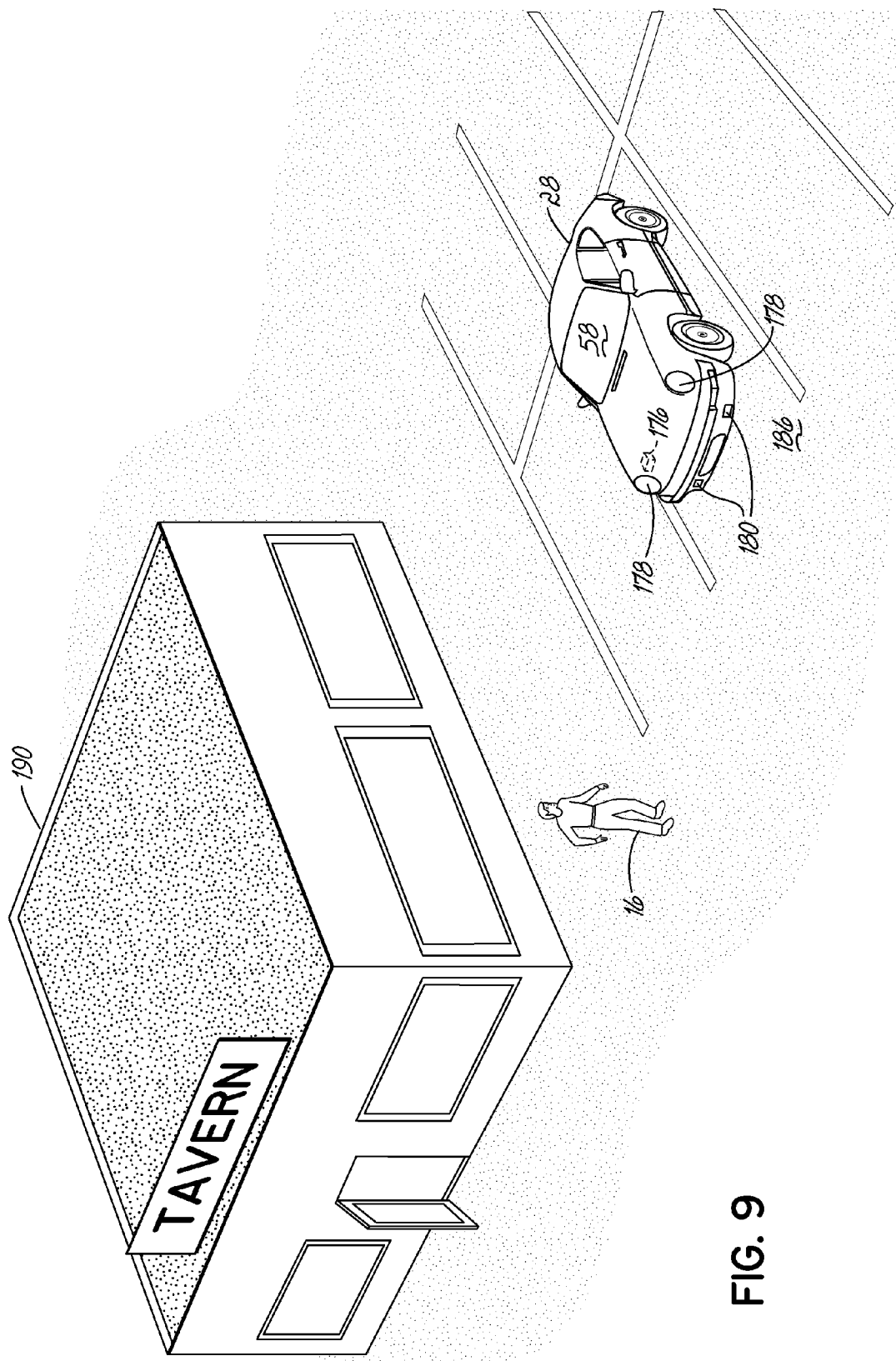
FIG. 9 is a perspective view showing the use of the present invention shown in FIGS. 1-4 in the context of a remote location test.

FIGS. 8 and 9 illustrate another application for an embodiment of the present invention in home confinement or in alcohol abstinence monitoring programs. Sometimes referred to as a "driveway test," the system 10 may be used to monitor a tester's 16 consumption or abstinence from alcohol without ever driving the vehicle 28. The ability to use the same impairment detection system 10 as both an interlock as well as an alcohol abstinence monitoring device can have significant cost savings. Such abstinence tests could be at random or set times during the day. In either case, the system 10 could be programmed to warm-up prior to the test to minimize the testing time. Additionally, the system 10 can record that a required test was not taken, if such happens to be the case. Finally, another advantage of using the system 10 for abstinence testing is that a tester 16, need not necessarily be confined to his or her house 120, but rather need only to be near their vehicle 28.

More specifically, in this program testing mode of operation, the control/relay module 30 will typically be programmed with three random test times during the day. These test times will typically be at least four but not more than eight hours apart. Each test time will typically allot a 15 minute window during which time the system 10 will power up and during which time the tester 16 will be notified of the random test. Every 3 minutes during this time period the horn 176 will sound once to remind the user 16 to come take a test. The vehicle's lights 178, 180 may also flash to alert the user 16 of a test. In alternative embodiments, a user 16 may be alerted that a test is required by a pager, cell phone, or other wireless devices. When 1 minute remains, the horn 176 will sound a plurality of times to let the tester 16 know time is running out. During this sequence, the handset 12 is in wait mode until the tester 16 gets videoed as would occur in a standard vehicle start sequence. At the end of the 15 minute period, if a test has not been conducted, a "No BAC Test Taken" violation is recorded in the CRM 30. The system 10 can further be configured to require it to be placed into early recall as a result of one or more such violations. In other words, in addition to recording a violation and when appropriate, preventing the vehicle 28 from starting, it should be appreciated that the user 16 may be alerted that he or she must return the system 10 to a monitoring facility within a certain time period, or the system 10 may go into lock-out mode, requiring the monitoring facility to "unlock" the vehicle. If the user 16 waits until the system 10 goes into lock-out mode, the vehicle 28 may have to be towed to the monitoring facility.

The system 10 can further be configured to allow for grace periods, for example, to allow a user to take a random test within 15 minutes of the expiration of the testing window. This will allow a user 16 who did respond to the random test, but was just late in getting to his or her vehicle 28, to not be penalized.

Figure 10:
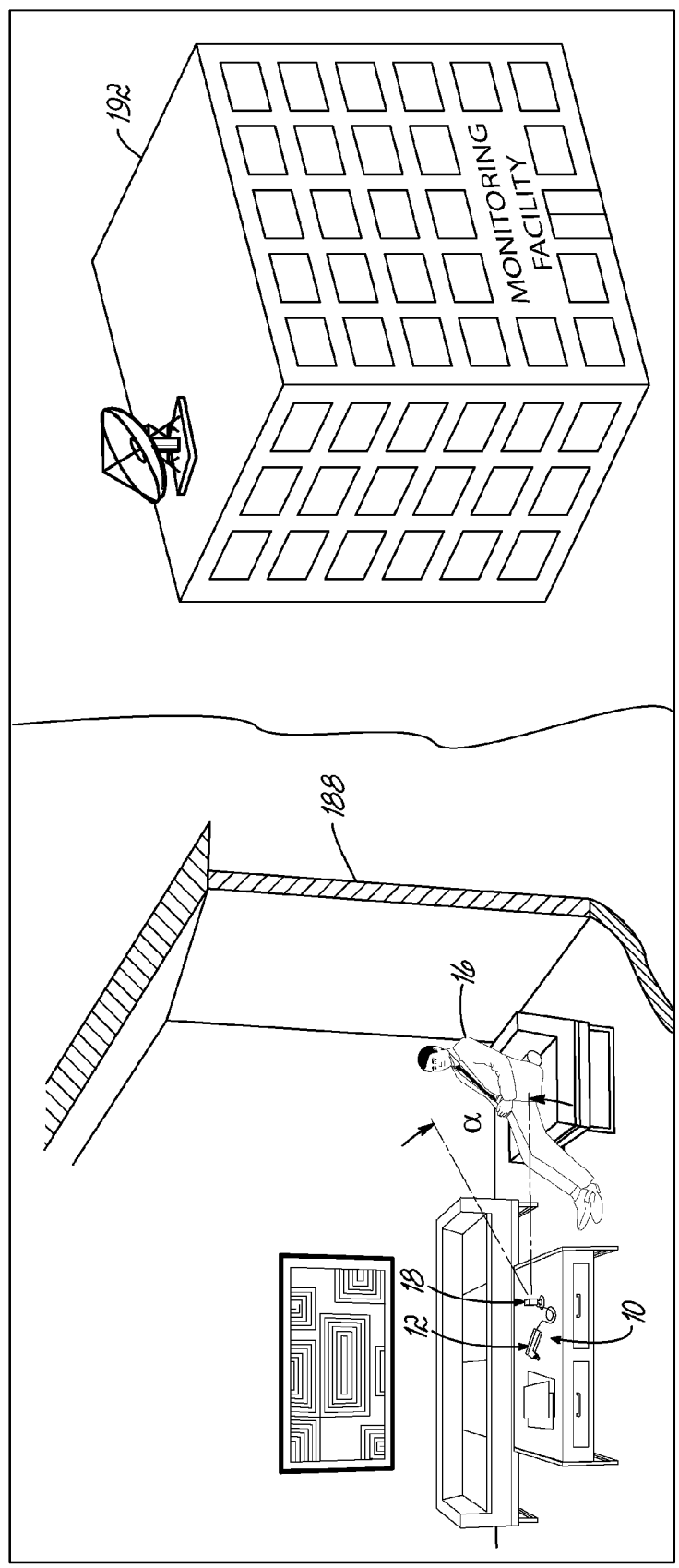
FIG. 10 is a perspective view of showing the use of the present invention shown in FIGS. 1-4 in the context of a home or business application.

While it is contemplated that many of the embodiments of the present invention will be used within a vehicle 28, and for program testing applications, that vehicle 28 may be parked in a user's 16 garage 182, driveway 184, or even in a parking lot 186, it is further contemplated that the other embodiments of the present invention could also be used in applications that do not necessarily involve vehicles. For example, as shown in FIG. 10, the system 10 could be configured to be used in a standalone application such as might be desirable for use in a home 188 where someone is under home confinement and is prohibited from consuming alcohol, or in a business 190 where the desire to monitor the alcohol absence of employees or patrons is desired. In these applications, the system 10 may be operatively connected to an external receiver or monitoring facility 192 via telephone, internet, secure PC connection, wireless growth path, or the like.

The present invention also encompasses a method of use of a chemical impairment detection system or a method for conducting a chemical impairment detection test comprising steps of surveying a chemical impairment detection test site location with a video surveillance system 18, the video surveillance system 18 having a camera with a lens 80 having a field of view 24 from which the camera views images. The method further includes determining whether a facial image of a tester 16 is properly positioned within the field of view 24 during the chemical impairment detection test. Finally the method includes the steps of prompting the tester 16 to provide a chemical impairment detection sample into a chemical impairment detection sampling device 12 and recording the facial image of the tester 16.

In alternative embodiments, the method may include the steps of sensing a positioning reference 128 by the video surveillance system 18, as well as tracking and analyzing the position reference 128 within the field of view 24. Additionally, the method may comprise the steps of receiving the breath-alcohol sample from the tester 16 via the mouth-piece 14 of a hand-held breath-alcohol sampling and analyzing device 12 and analyzing the sample. In other embodiments, the method may further comprise the step of transferring to an external receiver the chemical impairment detection result and the facial image of the tester 16. Other embodiments may also include the steps of alerting the tester 16 of a time window during which the chemical impairment test must be commenced and communicating with a vehicle ignition interlock 116 whether the tester 16 may start a vehicle 28. Finally, some methods may include the steps of starting a chemical impairment retest timer and initiating a chemical impairment retest.

The present invention also includes a method for reducing circumvention of a chemical impairment detection test comprising the steps of turning the ignition switch 118 of a vehicle 28 to the on position, activating a video surveillance system 18, and ensuring that a camera, located in the video surveillance system 18 is at a proper operating temperature. This method further includes the steps of detecting a position reference 128 located within a field of view 24 of the camera, prompting a tester 16 to begin blowing into a hand-held breath-alcohol sampling and analyzing device 12, and recording a facial image of the tester 16 during the chemical impairment detection test. Additionally, the method includes analyzing whether the position reference 128 remains within the field of view 24 of the camera during the chemical impairment detection test, determining whether the tester 16 provided a requisite breath-alcohol sample, and evaluating the breath-alcohol content of the breath-alcohol sample from the tester 16. Additionally, this method includes the steps of communicating to a vehicle ignition interlock 116 whether to allow the tester 16 to start the vehicle 28, monitoring the tester 16 during the operation the vehicle 28, and recording an image of the tester 16 during the operation of the vehicle 28. Finally, this method includes the steps of alerting the tester 16 of a time window during which a chemical impairment detection retest must be commenced and communicating the results of the chemical impairment detection test and the facial image of the tester 16 to an external receiver.

While the present invention has been illustrated by description of various embodiments and while these embodiments have been described in considerable detail, it is not the intention of the applicants to restrict or in any way limit the scope of the claims to such detail. Additional advantages and modifications will readily appear to those skilled in the art. The invention in its broader aspect is, therefore, not limited to the specific details, representative apparatus and method, and illustrative examples shown and described. Accordingly, departures may be made from such details without departing from the spirit or scope of the applicant's general inventive concept.

This has been a description of the present invention, along with the preferred method of practicing the invention currently known to the inventors. However, the invention itself should be defined only by the claims, Wherein we claim:

1. A chemical impairment detection system comprising:
a video surveillance system adapted to record a facial image of a tester, the video surveillance system having a camera with a lens having a field of view from which the camera views images, a control and relay module having a housing and a proper view and position determiner adapted to determine whether the facial image of the tester is properly positioned within the field of view during a chemical impairment detection test, and a test prompter to alert the tester when to begin the chemical impairment detection test; and
a chemical impairment detection sampling device in operable communication with and responsive to the video surveillance system, the sampling device adapted to receive a chemical impairment detection test sample from the tester.

2. The system of claim 1 wherein the chemical impairment detection sampling device has a positioning reference and wherein the video surveillance system is adapted to sense the positioning reference.

3. The system of claim 2 wherein the proper view and position determiner is adapted to track and analyze the positioning reference within the field of view.

4. The system of claim 3 wherein the chemical impairment detection sampling device is comprised of a hand-held breath-alcohol sampling and analyzing device having a mouth-piece for receiving a breath-alcohol sample.

5. The system of claim 4 wherein the positioning reference is a target that is located opposite the mouth-piece for receiving the breath-alcohol sample.

6. The system of claim 5 wherein the proper view and position determiner comprises non-transitory program code adapted to detect and track the target.

7. The system of claim 6 wherein the proper view and position determiner detects and tracks the target during the chemical impairment detection test.

8. The system of claim 7 further comprising a communication module in operable communication with an external receiver and adapted to facilitate the transfer of a chemical impairment detection test result and the facial image of the tester to the external receiver.

9. The system of claim 8 further comprising a test window alert to alert the tester of a time window during which the chemical impairment detection test must be commenced.

10. The system of claim 9 further comprising a vehicle ignition interlock that is in operable communication with the hand-held breath-alcohol sampling and analyzing device.

11. A method for conducting a chemical impairment detection test comprising:
surveying a chemical impairment detection test site location with a video surveillance system, the video surveillance system having a camera with a lens having a field of view from which the camera views images;
determining whether a facial image of a tester is properly positioned within the field of view during the chemical impairment detection test;
then prompting the tester to provide a chemical impairment detection sample into a chemical impairment detection sampling device; and
recording the facial image of the tester.

12. The method of claim 11 further comprising sensing a positioning reference by the video surveillance system.

13. The method of claim 12 further comprising:
tracking the position reference within the field of view; and
analyzing the position reference within the field of view.

14. The method of claim 13 further comprising receiving a breath-alcohol sample from the tester via a mouth-piece of a hand-held breath-alcohol sampling and analyzing device.

15. The method of claim 14 further comprising analyzing the breath-alcohol sample from the tester by the hand-held breath-alcohol sampling and analyzing device.

16. The method of claim 15 further comprising transferring to an external receiver a chemical impairment detection result and the facial image of the tester.

17. The method of claim 16 further comprising alerting the tester of a time window during which the chemical impairment test must be commenced.

18. The method of claim 17 further comprising communicating with a vehicle ignition interlock whether the tester may start a vehicle.

19. The method of claim 18 further comprising:
starting a chemical impairment retest timer; and
initiating a chemical impairment retest.

20. A method for reducing circumvention of a chemical impairment detection test comprising:
turning the ignition switch of a vehicle to the on position;
activating a video surveillance system;
ensuring that a camera, located in the video surveillance system is at a proper operating temperature;
detecting a position reference located within a field of view of the camera;
prompting a tester to begin blowing into a hand-held breath-alcohol sampling and analyzing device;
recording a facial image of the tester during the chemical impairment detection test;
analyzing whether the position reference remains within the field of view of the camera during the chemical impairment detection test;
determining whether the tester provided a requisite breath-alcohol sample;
evaluating the breath-alcohol content of the breath-alcohol sample from the tester;
communicating to a vehicle ignition interlock whether to allow the tester to start the vehicle;
monitoring the tester during the operation of the vehicle;
recording an image of the tester during the operation of the vehicle;
alerting the tester of a time window during which a chemical impairment detection retest must be commenced; and
communicating the results of the chemical impairment detection test and the facial image of the tester to an external receiver.

21. A method for conducting a chemical impairment detection test comprising:
surveying a chemical impairment detection test site location with a video surveillance system, the video surveillance system having a camera with a lens having a field of view from which the camera views images;
determining whether a facial image of a tester is properly positioned within the field of view during the chemical impairment detection test;
prompting the tester to provide a chemical impairment detection sample into a chemical impairment detection sampling device;
recording the facial image of the tester;
sensing a positioning reference by the video surveillance system;
tracking the position reference within the field of view;
analyzing the position reference within the field of view;
receiving a breath-alcohol sample from the tester via a mouth-piece of a hand-held breath-alcohol sampling and analyzing device;
analyzing the breath-alcohol sample from the tester by the hand-held breath-alcohol sampling and analyzing device;
transferring to an external receiver a chemical impairment detection result and the facial image of the tester;
alerting the tester of a time window during which the chemical impairment test must be commenced; and
communicating with a vehicle ignition interlock whether the tester may start a vehicle.

22. The method of claim 21 further comprising:
starting a chemical impairment retest timer; and
initiating a chemical impairment retest.

* * * * *